United States Patent [19]
Gordon et al.

[11] Patent Number: 5,744,014
[45] Date of Patent: Apr. 28, 1998

US005744014A

[54] STORAGE STABLE ELECTROLYTIC GAS GENERATOR FOR FLUID DISPENSING APPLICATIONS

[75] Inventors: John H. Gordon; Ashok V. Joshi; John McEvoy, all of Salt Lake City, Utah

[73] Assignee: Ceramatec, Inc., Salt Lake City, Utah

[21] Appl. No.: 685,303

[22] Filed: Jul. 23, 1996

Related U.S. Application Data

[63] Continuation-in-part of Ser. No. 300,947, Sep. 6, 1994, Pat. No. 5,538,605.
[51] Int. Cl.$^6$ .............................. C25B 9/00; C25B 11/02; C25B 11/12
[52] U.S. Cl. .................. 204/266; 204/271; 204/290 R; 204/291; 204/294
[58] Field of Search .................................. 204/263–266, 204/271, 290 R, 291, 294

[56] References Cited

U.S. PATENT DOCUMENTS

| | | | |
|---|---|---|---|
| 5,186,805 | 2/1993 | Gross et al. | 204/266 X |
| 5,242,565 | 9/1993 | Winsel | 204/266 X |
| 5,454,922 | 10/1995 | Joshi et al. | 204/266 X |
| 5,538,605 | 7/1996 | Joshi et al. | 204/266 |
| 5,567,287 | 10/1996 | Joshi et al. | 204/266 X |
| 5,593,552 | 1/1997 | Joshi et al. | 204/266 X |

*Primary Examiner*—Donald R. Valentine
*Attorney, Agent, or Firm*—Trask, Britt & Rossa

[57] ABSTRACT

An improved, gas-generating electrochemical cell utilizing a metal hydroxide containing cathode is disclosed. An electrolytic cell having an alkaline electrolyte, a metal hydroxide-containing cathode and a carbonaceous anode generator, a gas uniformly for use in a fluid delivery device. The cells and fluid delivery devices are sized to be particularly useful for delivery of small quantities of fluid over a prolonged period.

18 Claims, 6 Drawing Sheets

STORAGE STABLE ELECTROLYTIC GAS GENERATOR FOR FLUID DISPENSING APPLICATIONS

RELATED APPLICATION

This application is a continuation-in-part of application Ser. No. 08/300,947 filed Sep. 6, 1994 which issued as U.S. Pat. No. 5,538,605 on Jul. 23, 1996.

BACKGROUND OF THE INVENTION

1. Field of the Invention

The invention relates to a self-contained, storage stable, gas generating, electrolytic cell. The invention further relates to a dispensing device, in particular, a device where gas released from an electrochemical cell increases in pressure to press fluid from a bladder or syringe type fluid chamber through an outlet of the device in a steady continuous flow until the contents of the fluid chamber are exhausted.

2. State of the Art

Richter in U.S. Pat. No. 3,894,538 disclosed a device for dispensing medicines to man or beast. The medicine was contained in a flexible container which became compressed as fluid was electro-osmiotically introduced into an adjacent flexible chamber or when gas was electrolytically produced using precious metal electrodes and an unspecified fixed electrolyte. The rate of medicine discharge was to be regulated using a potentiometer.

Maget in U.S. Pat. No. 4,522,698 disclosed electrochemical prime movers. Embodiments of the invention include a device for dispensing pharmaceuticals to a human body over a substantial period of time at a sustained very low rate, where a battery provides the driving force to transport an electrochemically active gas from a precharged chamber to a second chamber, where an ion-exchange membrane separates the two chambers; or where the battery provides the driving force to transport oxygen from air across an ion-exchange membrane to a chamber. Pressure in a chamber increases as electroactive gas transports across the membrane, this increase in pressure drives a piston which forces the contained pharmaceutical fluid to flow through an outlet. The invention requires electrodes which are electrically conductive and act as catalysts to convert molecules to ions; titanium-palladium alloy or palladium black are recommended materials. A controller is utilized to control the magnitude and time pattern of current and voltage applied to the membrane as well as to turn current on and off. To function, the invention requires either exposure to air or precharging with an electroactive gas.

Maget in U.S. Pat. No. 4,886,514 disclosed electrochemically driven drug dispensers. A potential from an external power source drives an electrochemically active gas such as hydrogen or oxygen to be transported across a membrane from a fixed volume chamber to a chamber which has a variable volume. The volume of the chamber varies by either flexing an expansible diaphragm type wall or by displacing a sliding wall, said wall is shared by a second variable volume chamber which contains a fluid drug to be administered. As the electrochemically active gas is transported to the first variable volume chamber, the drug is forced out of the second variable volume chamber through an outlet. Countering the electrochemical transport of gas across the membrane, the gas diffuses in the opposite direction across the membrane in accordance to the pressure gradient and diffusivity properties of the membrane. A controller compensates for the gas diffusion rate and varies the voltage and current to achieve the desired drug delivery rate in a steady or intermittent mode. To function, the invention requires precharging with an electroactive gas.

Maget et al. in U.S. Pat. No. 4,902,278 disclosed a fluid delivery micropump. The pump utilizes an air-actuated battery in a fixed closed circuit with an electrochemical cell which drives the transport of oxygen in air across a membrane. The transport applies external pressure to a collapsible reservoir filled with fluid, as a result, fluid is expelled from the reservoir through an outlet. The membrane is preferably a Nafion material (a perfluoro sulfonic polymer) which has been coated with platinum black/10% Teflon. Electrodes are preferably titanium screens. To control the current, a resistor is utilized. The device is activated by removing a protective peel tab to expose air inlet ports to the battery cathode. A disadvantage of this type of system is that shelf life of the device is dependent on the integrity of the seals which prevent air leakage to the battery. If the seals are not perfect, the battery will slowly discharge before the desired time of use. To function, the invention requires exposure to air.

Winsel in U.S. Pat. No. 5,242,565 discloses a galvanic oxygen generating cell which is constructed much like a zinc/air button cell battery, where a reducible oxide is reduced at the cathode while hydroxyl ions are formed. Hydroxyl ions oxidize at the anode, releasing oxygen. A galvanic cell by definition is an electrochemical cell which requires no externally applied voltage to drive the electrochemical reactions. Disadvantages include the possibility of self discharge, premature release of gas, and low driving force—precluding the advantage of including a large resistor in the circuit to achieve a stable rate.

SUMMARY OF THE INVENTION

A storage stable, self-contained, gas-generating electrolytic cell has been invented. The cell is similar in construction and operation to the cell described in parent patent U.S. Pat. No. 5,538,605, by the same inventors. The cell contains an electroconductive anode, an aqueous electrolyte, and a cathode composed of an electrolytically decomposable chemical compound which produces a reduced metal when a voltage is applied.

An exemplary cell contains copper hydroxide as a principl component of the cathode. As electrical current passes through a circuit in which the cell is connected, copper is plated out in the cathode, and oxygen is released at the anode. To ensure storage stability, active cathode material is selected such that the cells require an applied voltage for the electrochemical reactions to proceed. A battery is provided in the circuit to drive the current through the gas generating cell. The rate of oxygen generated at the anode is in direct proportion to the current, and acts as a pressurizing agent to perform the work of expelling a fluid from a bladder or other fluid containing reservoir which has a movable wall which is acted upon as the gas is generated. The dispensed fluids may have some beneficial property such as medicinal, insecticidal, fragrant or other attributes.

DETAILED DESCRIPTION OF THE INVENTION

Figure 1:
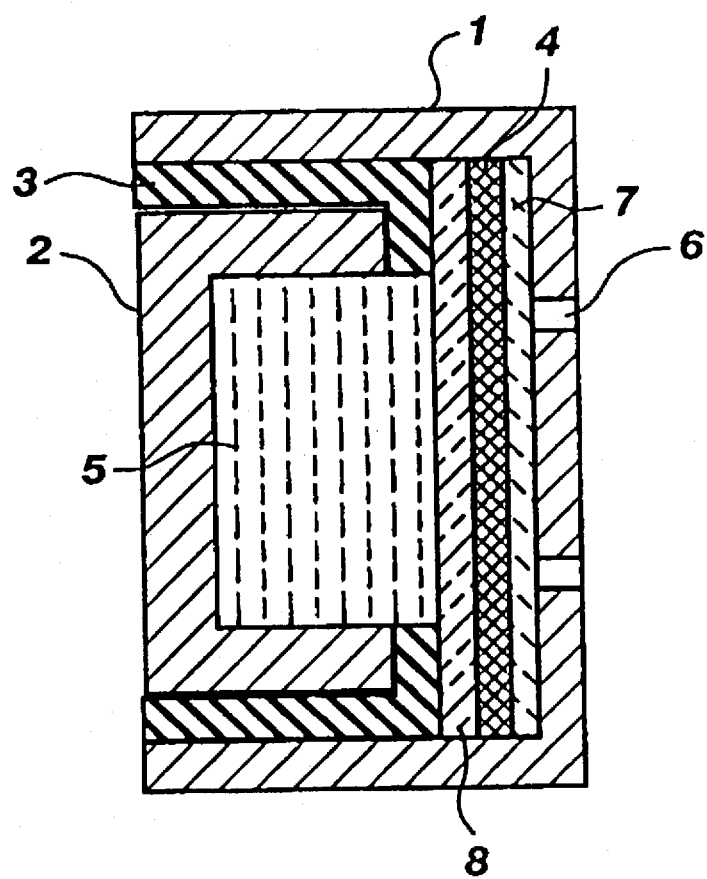
FIG. 1 is a schematic of the gas-generating, self-contained electrochemical cell employing a decomposable, hydroxyl ion producing chemical compound as a cathode material.

In an exemplary cell, the cathode chamber contains some aqueous electrolyte, which may be water, and a metal hydroxide or metal oxide. In general, there is a preference for metal hydroxide over metal oxide since the former is more electroactive. The metal hydroxide and metal oxide have general compositions $M_a(OH)_b$ and $M'_xO_y$, respectively, where M and M' are metallic elements with oxidation states $+(b/a)$ and $+(y*2/x)$. Examples of metal hydroxides and metal oxides include: $Cu(OH)_2$, $CuO$, $Ni(OH)_2$, $NiO$, $Bi(OH)_3$, $Bi_2O_3$, $Pb(OH)_2$, $PbO$, $Mn(OH)_2$, $MnO$, $Hg(OH)_2$, $HgO$, $Cr(OH)_3$, $Cr_2O_3$, $Zn(OH)_2$, $ZiO$, $Sn(OH)_2$, and $SnO$. The overall reactions in the cell as it generates oxygen are:

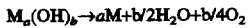

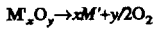

A gelling or suspension agent, for example carboxymethyl cellulose and the like may be added to the electrolyte to improve manufacturability but is not otherwise required. The cathode material is contained in a chamber of the cell which has some portion which is electronically conductive and which may be placed in electronic communication with an electronic circuit such that upon completing the electrical circuit, the cathode is connected to the negative pole of the power source.

Depending on the electronic conductivity of the metal hydroxide or oxide, a separator between the cathode material and the anode may be required. For several metal hydroxides such as copper hydroxide, a separator is not required. An electronically conductive material such as carbon black or graphite may be added to the metal hydroxide (oxide)/ electrolyte mixture. In this case a separator is required regardless of the electronic conductivity of the metal hydroxide or oxide. The separator must be electronically insulating, ionically conductive, and moisture permeable. Several thin films with such characteristics are commercially available such as hydrophilic microporous membranes made of polystyrene or polyolefin. The anode is comprised of electronically conductive and hydrophobic materials. An exemplary anode consists of high surface area carbon which has been coated to some degree with a hydrophobic material such as polytetrafluoroethylene (PTFE) to make it hydrophobic. The coated carbon typically is pressed into a metal screen or expanded metal which serves as a current collector. The electronically conductive anode is in electronic communication with an electronic circuit but not in direct contact with electronically conductive material in the cathode. If the electrolyte is alkaline, an expanded metal nickel plated steel screen is very effective as an anode without carbon being present. Between the cell gas exit port(s) and the anode it is desirable to provide additional protection to prevent the loss of moisture of electrolyte as the cell generates gas. A film of PTFE or FEP between the gas exit port(s) and the anode is required for this purpose. If the device is to have low rate, it may be possible to utilize a sintered film which has lower moisture permeability to increase the storage stability. If the device is to have a high pump rate, then a nonsintered film which is very hydrophobic but microporous is preferred. To gain the same low moisture retention protection, a metal foil, metallized plastic film or a sintered PTFE or FEP film with adhesive may be placed over the gas port(s). An adhesive is selected such that the film will release when the cell begins to operate after activation and build up of internal pressure. The moisture barrier is very important for long shelf life since the loss of internal moisture due to evaporation will change the performance of the cell or in the extreme make the cell nonfunctionable.

If it is desirable to have a gas mixture driving the fluid delivery device which is not solely oxygen, then it is possible to get nitrogen gas or carbon dioxide gas in addition to oxygen by respectively adding a reducible nitride or a carbonate to the cathode mixture. For example, the addition of TiN to a cathode mixture containing copper hydroxide yields a mixture of oxygen and nitrogen gas to drive the device.

FIG. 1 shows a schematic representation of a cell. The cell is constructed in similar fashion to a zinc/air type button cell battery. The cylindrical outer can 1 serves as an anode contact and contains the cell. The cylindrical cap 2 is the cathode member and cathode contact and partially contains the cathode mixture. It is sometimes desirable to construct the cap or have it clad or plated with the metal which will be plating out during operation of the cell. For example if $Cu(OH)_2$ is the active cathode material, then it is desirable to have the cap clad or plated at least on the inside with copper or to construct the cap with metallic copper. This is because the cell, as it begins to generate gas, immediately causes plating onto a like metal surface whereas if the inner cap surface were stainless steel or nickel, a dissimilar metal, a delay occurs. This phenomenon may not be true for all potential cathode materials but is at least true for copper. In the case of copper, the phenomenon is believed to occur because of disproportionation which occurs between the $Cu^{++}$ ion and metallic Cu before the cell is activated. Since it is believed that the formation of $Cu^+$ is part of the mechanism for plating, the disproportionation may set up the plating pathway before the cell is activated.

Between can 1 and cap 2 is an electronically and ionically insulating material which is the grommet 3. The grommet is typically made of nylon and serves as a sealing gasket between the can and cap as well as insulator. The cap and can are crimped together to form a seal. The anode 4 is in electronic communication radially with the can, and is in ionic communication with the cathode mixture 5 which is primarily contained within the cap. To promote the passing of gas through the gas port(s) 6 located in the bottom of the can, the anode 4 is in intimate contact with the hydrophobic barrier 7. The hydrophobic barrier typically is a PTFE or FEP film either sintered or unsintered 0.002–0.008 inches thick. Typically, a separator 8 electronically isolates the anode 4 from the cathode mixture 5. The separator is required if the mixture includes any electronically conductive constituents such as carbon or graphite.

Figure 2D:
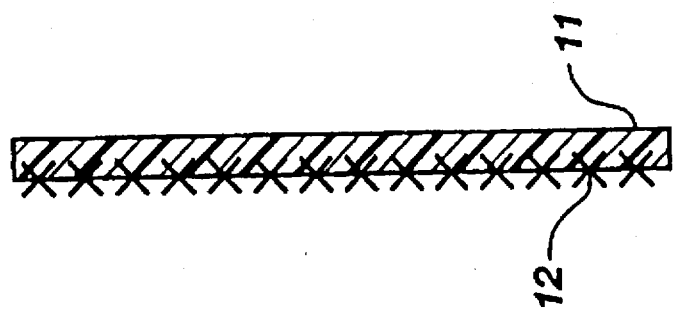
FIGS. 2A–D are schematic representations of different anode configurations which may be utilized in the gas-generating cell depicted in FIG. 1.
Figure 2C:
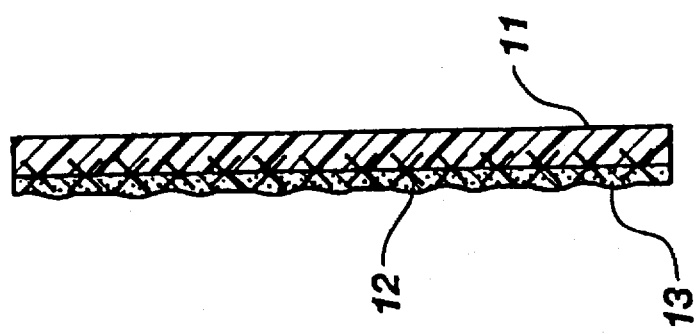
Figure 2B:
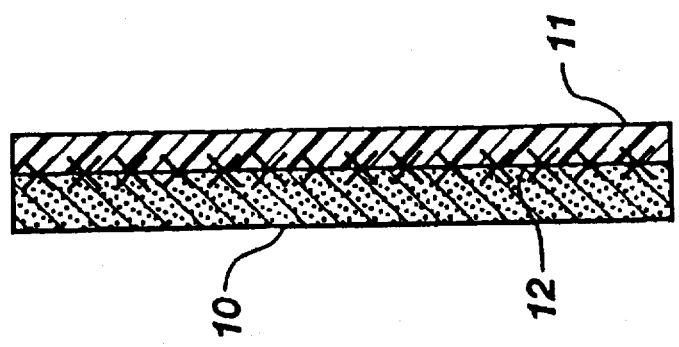
Figure 2A:
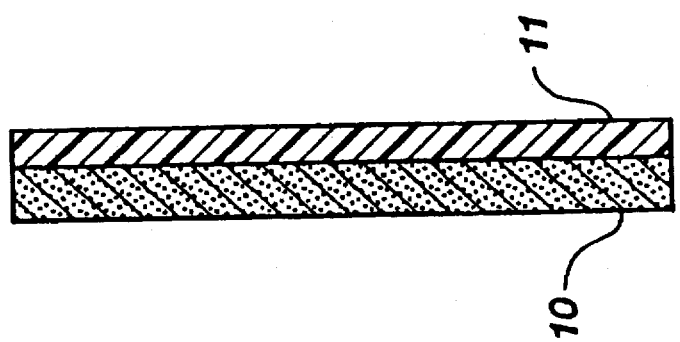

FIGS. 2A–2D schematically show several possible configurations of the anode 4. As shown in 2A, it may consist of a mixture of carbon and/or graphite sintered together with PTFE or FEP to form an electronically conductive film 10 which is electrochemically active and somewhat hydrophobic. This film is laminated using pressure to a nonsintered PTFE or TFE film 11. As shown in FIG. 2B, the anode may be similar to 2A except the films may be laminated to a metallic mesh, expanded metal or screen to serve as a current collector 12 therebetween. This configuration makes better contact radially with the can. As shown in FIG. 2C, the anode may consist of a mixture of carbon and/or graphite 13 which has been coated with PTFE or FEP and pressed into a metallic mesh, expanded metal or screen to serve as a current collector and laminated using pressure to a nonsintered PTFE or TFE film 11. As shown in FIG. 2D, the anode may be simply a metallic mesh, expanded metal or screen and co-laminated to a nonsintered PTFE or FEP film.

Figure 3:
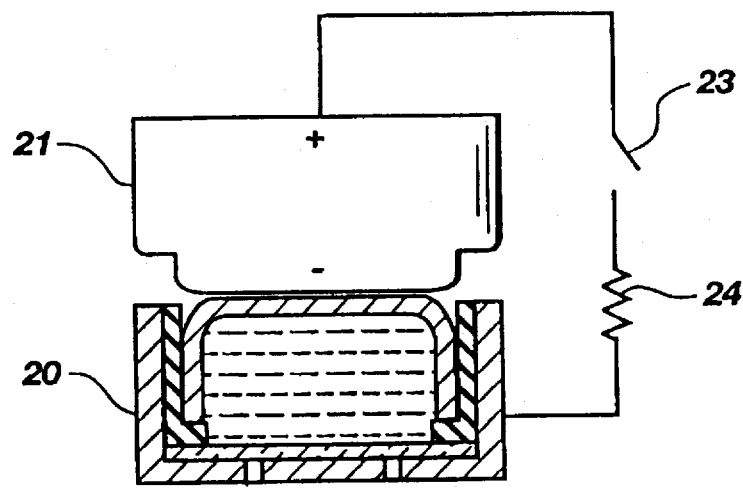
FIG. 3 is a schematic of the gas-generating, self-contained electrochemical cell as shown in FIG. 1 which has been integrated with a battery power source.

FIG. 3 schematically shows the electrical circuit required to make the cell functional. The gas cell is referred generally as 20. The cell may be placed in direct contact with a direct current voltage source such as a button cell battery 21. One or more batteries may be utilized. The rate of the device will be determined by the voltage provided by the batteries and the resistance of the resistor in the circuit. A convenient configuration is to affix the gas cell to the battery using an electronically conductive adhesive. The negative contact of the battery is in electrical communication with the gas cell cap which is in communication with the cathode. The circuit also includes a switch 23 and resistor 24.

Figure 4:
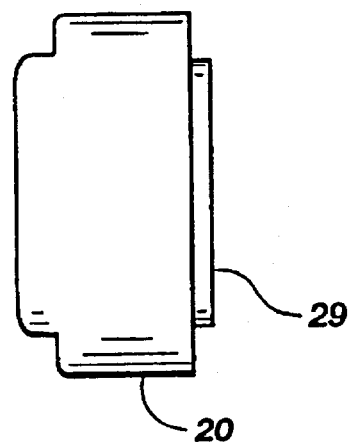
FIG. 4 is a schematical representation of a releasable moisture barrier to increase the storage life of the cell depicted in FIG. 1.

FIG. 4 shows a releasable moisture barrier 29 covering the gas outlet port(s). Such a barrier can be utilized if the device requires long shelf life, but also requires a high rate during operation. The releasable moisture barrier may be metal foil with adhesive which releases under the pressure initially generated when the device is activated. Other suitable materials would include metallized plastic films, PCTFE, or sintered PTFE or FEP.

Figure 5A:
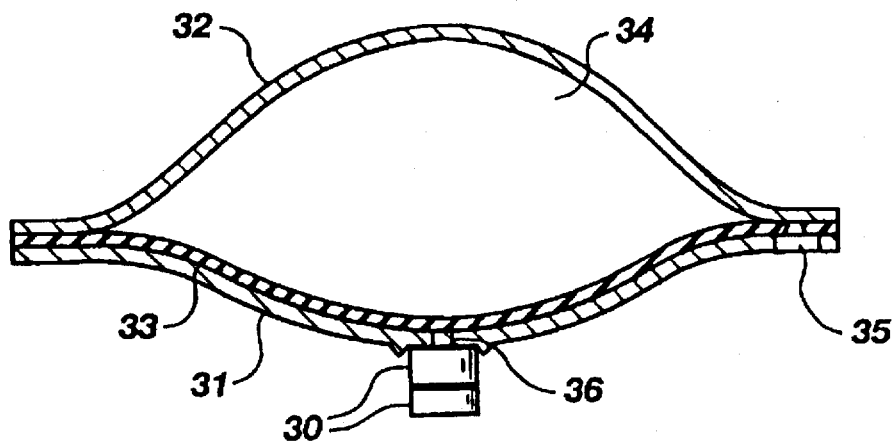
FIG. 5 is a schematic illustration of a bladder type fluid dispensing apparatus employing a gas-generating cell of the type illustrated in FIG. 3.
Figure 5B:
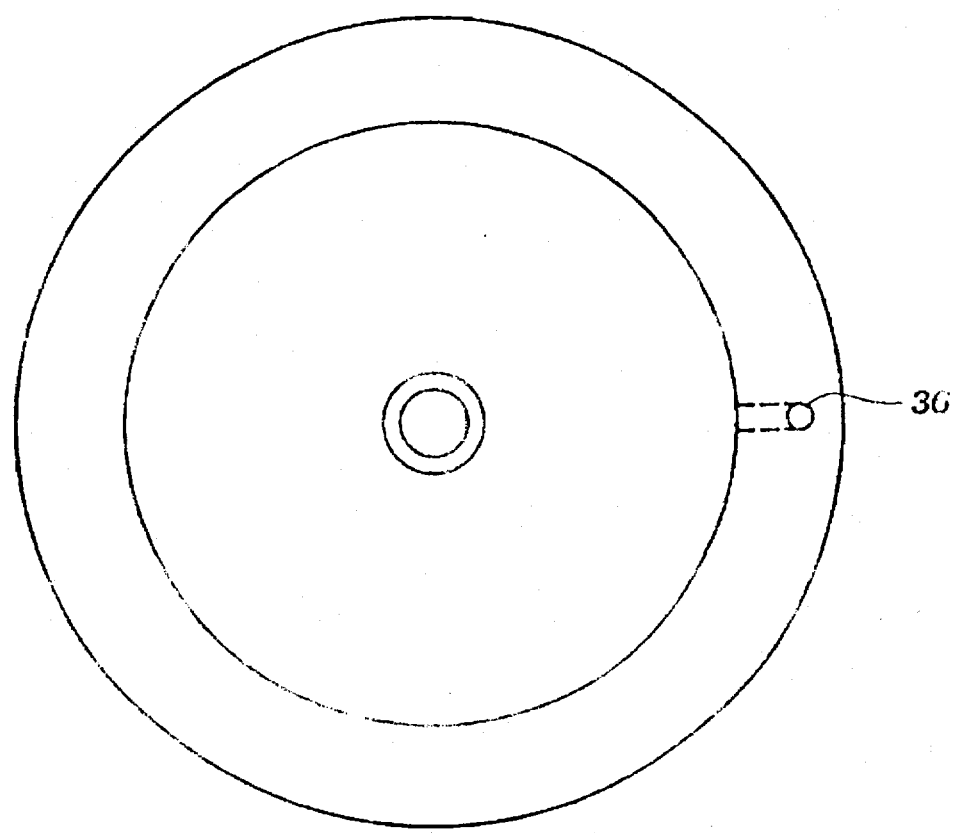

FIG. 5 schematically shows the gas cell and battery, referred to collectively as item 30, attached to a two-chamber, bladder-type fluid dispensing reservoir. The bladder reservoir consists of a gas chamber outer shell 31, and a fluid chamber outer shell 32, with a flexible diaphragm 33 therebetween. A gas tight seal is made at the perimeter between the diaphragm and the gas chamber outer shell 31. Similarly, a liquid tight seal is made at the perimeter of the diaphragm 33 and the fluid outer shell 32. Initially, fluid fills the fluid chamber 34. To activate the device, a puncture is made in the diaphragm at fluid outlet 35 and the electrical switch in the circuit (which is not shown) is completed.

Upon activation, gas is generated in the gas cell, flows through the cell gas port(s) 6, and through the reservoir gas port 36. The diaphragm is pushed by the gas away from the gas chamber outer shell 31 to form the gas chamber. Simultaneously fluid flows out of fluid outlet 35 at a rate directly proportional to the rate of gas generation, which is directly proportional to the current in the circuit.

Figure 6:
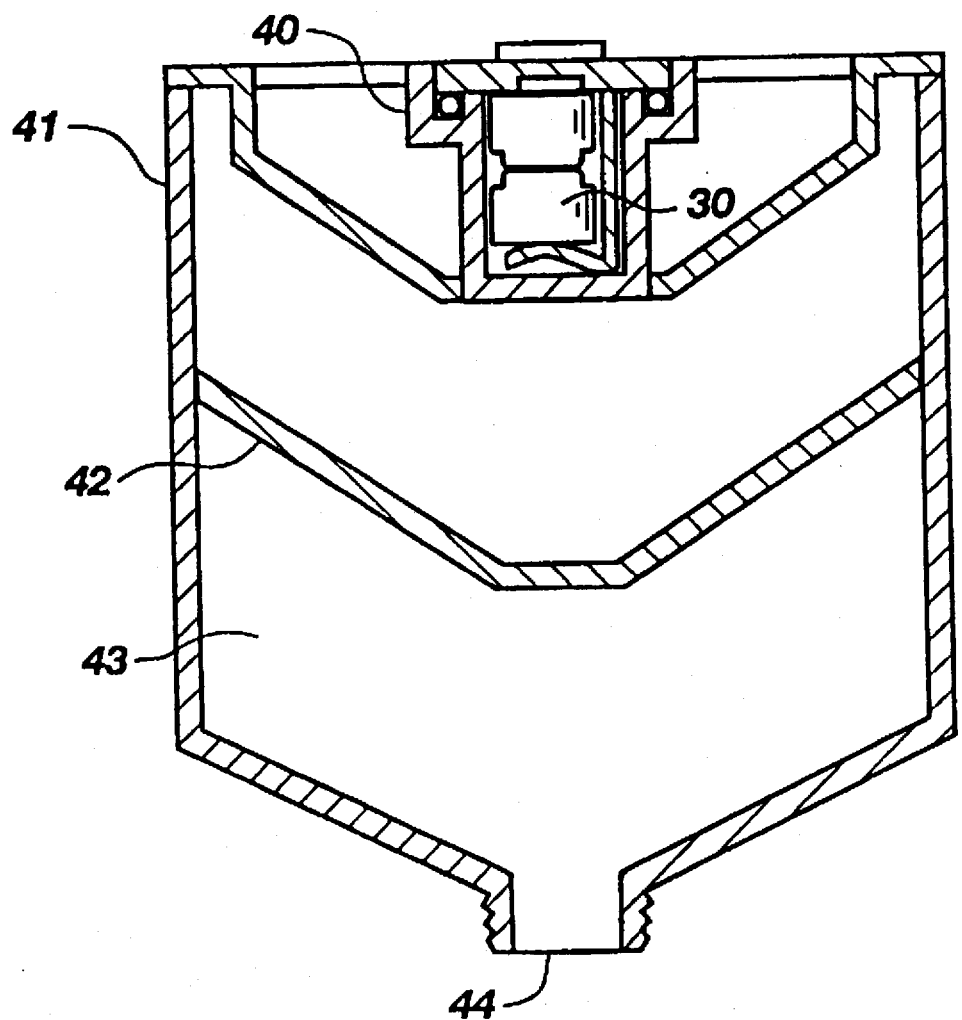
FIG. 6 is a schematic illustration of a plunger type fluid dispensing apparatus employing a gas-generating cell of the type illustrated in FIG. 3.

FIG. 6 shows schematically a plunger type fluid delivery device. The gas cell and battery, referred together as item 30, are in a module 40 which includes the components of a multiple setting switch. The module is integrated to the housing 41 which is gas tight except for fluid outlet 44 and an opening for gas from the module. Fluid 43 is contained between the housing and the plunger 42. The plunger initially is tight against the upper portion of the housing near the module. When the switch is turned to an "on" setting, gas from the gas cell pushes the plunger which in turn pushes the fluid out of the housing.

EXAMPLE 1

A cell was constructed similar to the configurations shown in FIG. 1, FIG. 2D, and FIG. 3 and was used to drive a fluid dispensing device as shown in FIG. 5. The can was constructed of nickel plated steel. The cap was a tri-clad material of nickel, steel, and copper, wherein copper was the surface metal on the inside of the cap. The cathode mixture contained 30% copper hydroxide, 7.5% graphite powder, 25% sodium hydroxide, and 37.5% water. A Cellguard 5511 separator, which is a hydrophilic microporous polyolefin membrane separator, from Hoerchst Celanese was utilized against an anode which was nickel plated steel expanded metal mesh which had been dipped in a Teflon T30 slurry and dried, then pressed to a 0.004 inch thick unsintered Teflon film from Fluorglas. The grommet was made of nylon 6/6. A hydrophobic barrier of 0.002 inch sintered Teflon film was located between the anode and the gas ports. The gas cell was driven with a 393 silver oxide battery from Eveready and the circuit included an 11,000 ohm resistor. The bladder type reservoir contained 9 cc of fluid. During operation, the rate of fluid delivery was nearly constant at the rate of 0.2 cc per day until the bladder was completely empty.

Cells having cathodes which have copper hydroxide as the principal metal constituent are generally preferred. A cathode paste of the following composition is quite useful:

| Constituent | Range (% by wt.) |
|---|---|
| $Cu(OH)_2$ | 20–45% |
| Graphite | 3–12% |
| NaOH | 0–35% |
| Water | 25–50% |

A preferred cathode paste has the following composition:

| Constituent | Range (% by wt.) |
|---|---|
| $Cu(OH)_2$ | 20–40% |
| Graphite | 5–10% |
| NaOH | 20–30% |
| Water | 30–45% |

Cells having optimum performance in terms of gas generation, endurance and predictability have cathode pastes of the following especially preferred composition:

| Constituent | Range (% by wt.) |
|---|---|
| $Cu(OH_2)$ | 28–36% |
| Graphite | 7–9% |
| NaOH | 22–26% |
| Water | 33–39% |

The devices described herein work especially well in an alkaline electrolyte and generally operate optimally at a pH greater than about 8 with operation at a pH greater than about 9 being advantageous.

Figure 7:
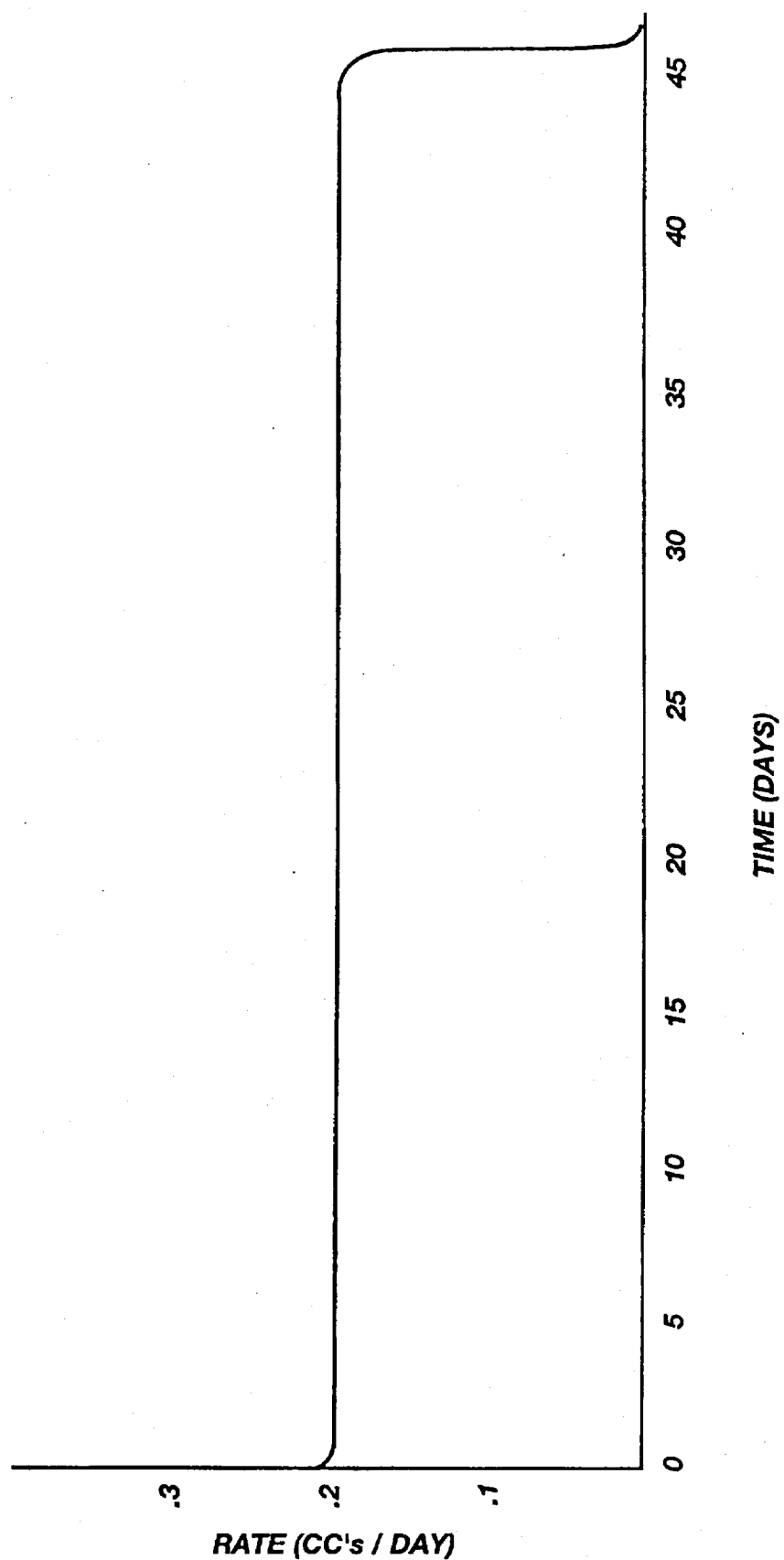
FIG. 7 is a fluid dispensing rate graph for the system of example 1.

FIG. 7 shows a plot of fluid dispensed over time using the device described in Example 1.

What is claimed is:

1. A storage stable gas-generating electrolytic electrochemical cell comprising
    a sealed cathode compartment containing a cathode mixture including an aqueous electrolyte and a reducible metal hydroxide or metal oxide;
    a cathode member associated with said cathode compartment;
    an anode compartment having at least one gas outlet port and an anode member;

a hydrophobic barrier film between said anode member and gas outlet port(s)

a power supply having its negative pole communicating with said cathode member and its positive pole communicating with said anode member; and a moisture barrier during storage between the anode member and the environment, wherein said anode member consists of a mixture of carbon and/or graphite sintered together with a hydrophobic polymeric material to form an electronically conductive film which is electrochemically active and somewhat hydrophobic and where this film is laminated to a nonsintered hydrophobic polymeric film.

2. The gas-generating cell of claim 1, wherein said reducible metal hydroxide is a hydroxide of Cu, Ni, Pb, Hg, Sn, Zn, Mn, or Bi.

3. The gas-generating cell of claim 1, wherein said reducible metal hydroxide is an hydroxide of Cu, Ni, Pb, Hg, Sn, Zn, Mn, or Bi.

4. The gas-generating cell of claim 1, wherein said anode member consists of a mixture of carbon and/or graphite sintered together with hydrophobic polymeric material to form an electronically conductive film which is electrochemically active and somewhat hydrophobic and where this film is laminated to a nonsintered hydrophobic polymeric film.

5. The gas-generating cell of claim 1, wherein said anode member consists of of a mixture of carbon and/or graphite which have been coated with hydrophobic polymeric material and pressed into a metallic mesh, expanded metal or screen to serve as a current collector.

6. The gas-generating cell of claim 1, wherein said anode member consists of a metallic mesh, expanded metal or screen and co-laminated to a nonsintered hydrophobic polymeric film.

7. The gas-generating cell of claim 1, wherein said electrolyte is alkaline.

8. The gas-generating cell of claim 1, wherein said cathode mixture includes a reducible nitride.

9. The gas-generating cell of claim 8, wherein said reducible nitride is TiN.

10. The gas-generating cell of claim 1, wherein said cathode mixture includes a carbonate.

11. The gas-generating cell of claim 1, wherein a separator is between said cathode mixture and said anode member consisting of a film which is electronically insulating, ionically conductive and moisture permeable.

12. The gas-generating cell of claim 11, wherein said cathode mixture includes an electronic conductive material.

13. The gas-generating cell of claim 12, wherein said electronically conductive material in said cathode mixture is carbon or graphite.

14. The gas-generating cell of claim 1, wherein said voltage source is one or more batteries.

15. An electrically self-contained, fluid-dispensing pump comprising:

a gas-generating cell as defined in claim 1;

a fluid chamber adapted to contain a fluid, said fluid chamber having a fluid discharge outlet;

a gas chamber adapted to contain a gas, said gas chamber having a duct communicating with said gas-generating cell; and a movable wall which is common to both said fluid chamber and said gas chamber.

16. An electrically self-contained fluid-dispensing pump of claim 15, wherein said movable wall is a flexible diaphragm.

17. An electrically self-contained fluid-dispensing pump of claim 15, wherein said movable wall is a plunger.

18. The gas-generating cell of claim 1, wherein said metal hydroxide is copper hydroxide.

* * * * *

UNITED STATES PATENT AND TRADEMARK OFFICE
CERTIFICATE OF CORRECTION

PATENT NO. : 5,744,014
DATED : April 28, 1998
INVENTOR(S) : John H. Gordon, et al.

It is certified that error appears in the above-identified patent and that said Letters Patent is hereby corrected as shown below:

Col. 2, line 45          Delete principl and insert instead -- principal --.

Col. 5, line 38          Delete "," after 31 and insert -- and --.

Signed and Sealed this

Third Day of November, 1998

Attest:

BRUCE LEHMAN

*Attesting Officer*        *Commissioner of Patents and Trademarks*

UNITED STATES PATENT AND TRADEMARK OFFICE
CERTIFICATE OF CORRRECTION

PATENT NO. : 5,744,014
DATED : April 28, 1998
INVENTOR(S) : Gordon et al.

It is certified that error appears in the above-identified patent and that said Letters Patent is hereby corrected as shown below:

On the title page, in item [56], References Cited, insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 4 | 2 | 3 | 4 | 5 | 4 | 06/13/95 | Lippmann | | | , |
| | | 5 | 5 | 7 | 3 | 6 | 4 | 6 | 11/12/96 | Saito et al. | | | |
| | | | | | | | | | | | | | |

OTHER DOCUMENTS

| | | |
|---|---|---|
| | International Search Report dated 17 November 1997. |
| | |

Signed and Sealed this

Thirteenth Day of April, 1999

*Attest:*

Q. TODD DICKINSON

*Attesting Officer*     *Acting Commissioner of Patents and Trademarks*